United States Patent
Zirps

[19]

[11] Patent Number: 6,053,907
[45] Date of Patent: Apr. 25, 2000

[54] SURGICAL INSTRUMENTS WITH FLEXIBLE DRIVE SHAFT

[75] Inventor: Christopher Zirps, Milton, Mass.

[73] Assignee: Endius Incorporated, Plainville, Mass.

[21] Appl. No.: 09/133,754

[22] Filed: Aug. 13, 1998

[51] Int. Cl.$^7$ ................................................. A61B 17/36
[52] U.S. Cl. ............................... 606/1; 606/108; 604/20
[58] Field of Search ....................... 606/1, 14, 15, 606/16, 17, 10, 11, 12, 108, 170, 180; 604/20, 21, 22, 167

[56] References Cited

U.S. PATENT DOCUMENTS

| | | | |
|---|---|---|---|
| 5,281,231 | 1/1994 | Rosen et al. | 606/15 |
| 5,522,815 | 6/1996 | Durgin, Jr. et al. | 604/21 |
| 5,575,787 | 11/1996 | Abela et al. | 606/15 |
| 5,607,419 | 3/1997 | Amplatz et al. | 606/15 |
| 5,743,905 | 4/1998 | Eder et al. | 606/32 |
| 5,814,062 | 9/1998 | Sepetka et al. | 606/108 |

*Primary Examiner*—Linda C. M. Dvorak
*Assistant Examiner*—Sonya Harris-Ogugua
*Attorney, Agent, or Firm*—Tarolli, Sundheim, Covell, Tummuno & Szabo L.L.P.

[57] ABSTRACT

A drive shaft (16) for a surgical instrument (10) has a rigid drive shaft section (30) having an end portion (32). A flexible drive shaft section (40) comprises a bendable spring having an outer surface (44) and an end portion (42). The instrument (10) also comprises a sleeve (50) having an inner surface (52) and extending from the end portion (32) of the rigid drive shaft section (30) over the end portion (42) of the flexible drive shaft section (40). The instrument (10) further comprises an adhesive material (60) joining the inner surface (52) of the sleeve (50) to the outer surface (44) of the bendable spring (40).

13 Claims, 2 Drawing Sheets

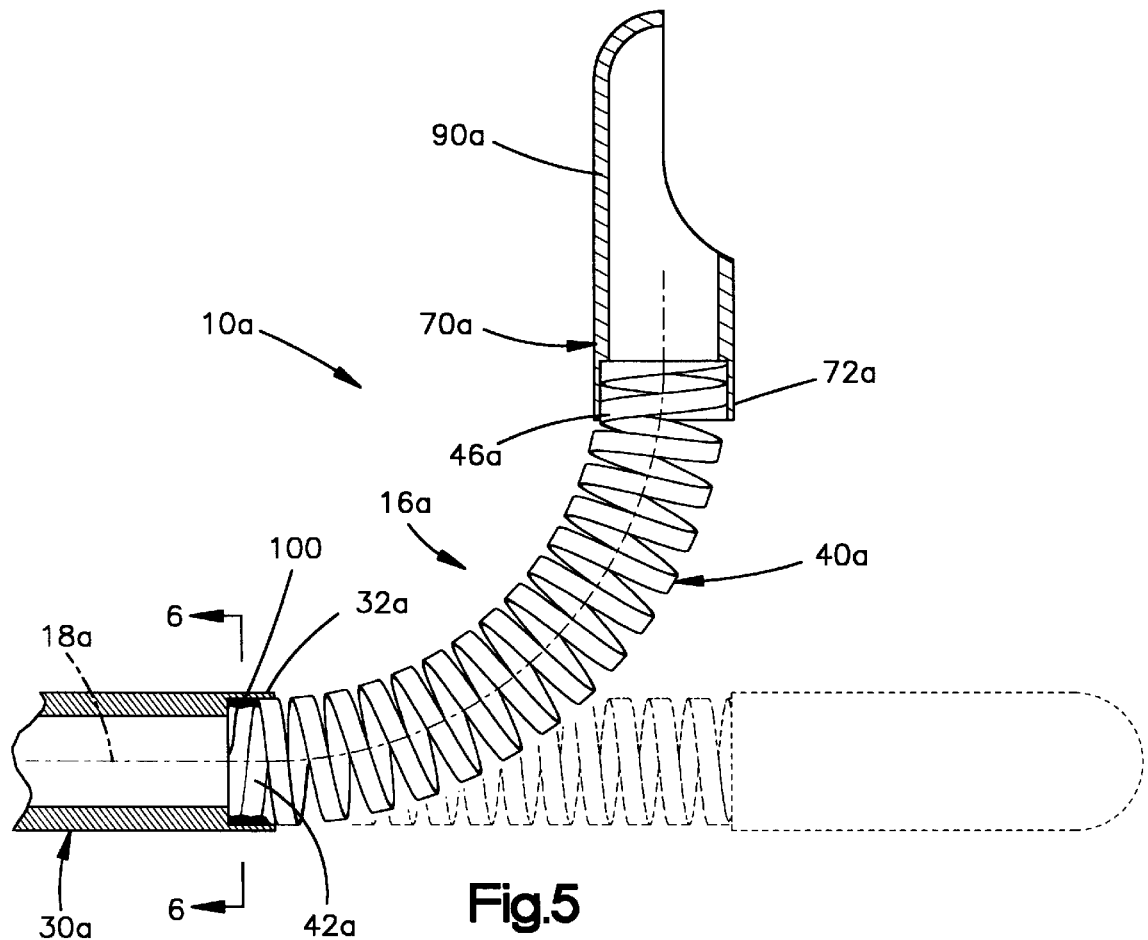
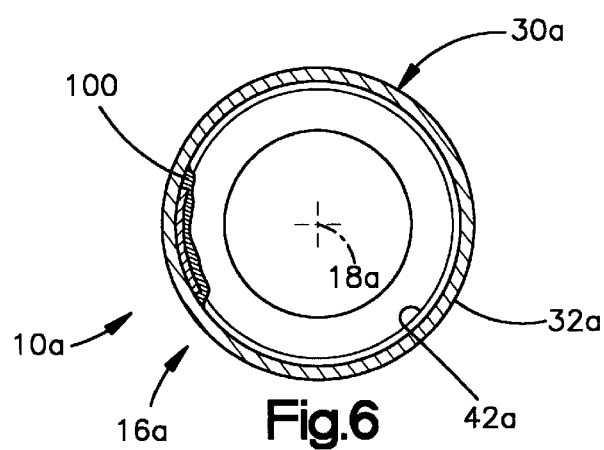

SURGICAL INSTRUMENTS WITH FLEXIBLE DRIVE SHAFT

BACKGROUND OF THE INVENTION

The present invention relates to a surgical instrument and more particularly to an arthroscopic or endoscopic surgical instrument which may be used to remove or otherwise treat tissue.

Some surgical instruments of this type have flexible drive shafts. The flexible drive shaft includes a flexible section that is joined at each end to a rigid section or a rigid cutting tool. The flexible section is commonly a spring made of a cold-worked metal and the rigid sections are also made of metal. The parts are joined by welding. In some cases the cold-worked metal spring can lose its strength in the vicinity of the weld. Also, the spring can become distorted by the heat of the welding process. The loss of spring strength in the vicinity of the weld can cause the spring to break at unacceptably low driving torque.

SUMMARY OF THE INVENTION

The present invention is a surgical instrument drive shaft comprising a rigid drive shaft section having an end portion. A flexible drive shaft section comprises a bendable spring having an outer surface and an end portion. The instrument also comprises a sleeve having an inner surface and extending from the end portion of the rigid drive shaft section over the end portion of the flexible drive shaft section. The instrument further comprises an adhesive material joining the inner surface of the sleeve to the outer surface of the bendable spring.

BRIEF DESCRIPTION OF THE DRAWINGS

FIG. 5 is a view similar to FIG. 2 of a surgical instrument constructed in accordance with a second embodiment of the present invention; and FIG. 6 is a sectional view taken along line 6—6 of FIG. 5.

DESCRIPTION OF PREFERRED EMBODIMENTS OF THE INVENTION

Figure 1:
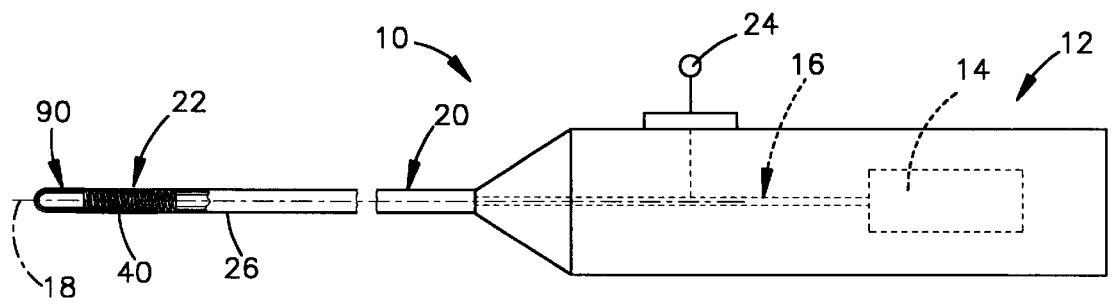
FIG. 1 is a schematic illustration of a surgical instrument constructed in accordance with the present invention, shown in a linear or straight condition.

The present invention relates to a surgical instrument and more particularly to an arthroscopic or endoscopic surgical instrument which may be used to remove or otherwise treat tissue. As representative of the present invention, FIG. 1 illustrates a surgical instrument 10.

The surgical instrument 10 includes a handle 12 which houses a motor 14. A drive shaft 16 is connected with the output of the motor 14. The drive shaft 16 is rotatable about a longitudinal central axis 18 of the surgical instrument 10.

Figure 2:
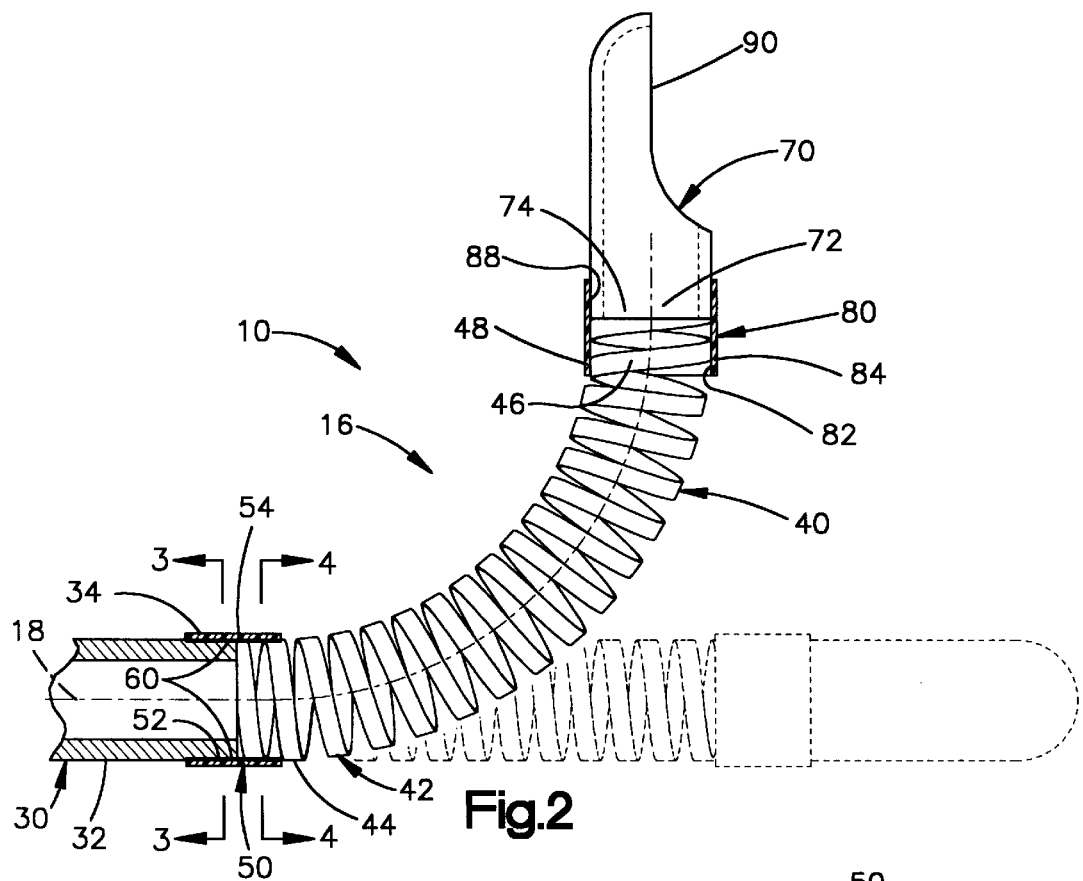
FIG. 2 is a longitudinal sectional view of a portion of the surgical instrument of FIG. 1, shown in a bent condition.

The surgical instrument 10 has a rigid stem section 20, a flexible stem section 22, and a deflection control assembly 24 for controlling bending movement of the flexible stem section 22. The deflection control assembly 24 is operable in a known manner (not shown), such as by wires, to effect bending movement of the flexible stem section 22 to a condition off the axis 18, as shown in FIG. 2, for example. A sheath 26 (shown in FIG. 1 only) encloses the rigid and flexible stem sections 20 and 22.

The drive shaft 16 has a rigid tubular section 30 (FIG. 2) which forms part of the rigid stem section 20 of the surgical instrument 10, and a flexible section 40 forming part of the flexible stem section 22 of the surgical instrument. The rigid drive shaft section 30 has a distal end portion 32. The distal end portion 32 of the rigid drive shaft section has a cylindrical outer surface 34.

The flexible drive shaft section 40 is a cold-worked helically coiled spring preferably made from surgical stainless steel strip having a rectangular cross-section. The flexible drive shaft section 40 has a proximal end portion 42 with a cylindrical outer surface 44. The flexible drive shaft section 40 also has a distal end portion 46 with a cylindrical outer surface 48. The flexible drive shaft section 40 is shown in solid lines in FIG. 2 as bent 90 degrees from its linear position which is shown in dashed lines in FIG. 2.

The proximal end portion 42 of the flexible drive shaft section 40 is connected by a plastic sleeve 50 for rotation with the distal end portion 32 of the rigid drive shaft section 30. The plastic sleeve 50 has a hollow cylindrical configuration including parallel, cylindrical inner and outer surfaces 52 and 54. The inner surface 52 of the sleeve 50 is bonded to the outer side surface 34 of the distal end portion 32 of the rigid drive shaft section 30 and to the outer side surface 44 of the proximal end portion 42 of the flexible drive shaft section 40.

Figure 3:
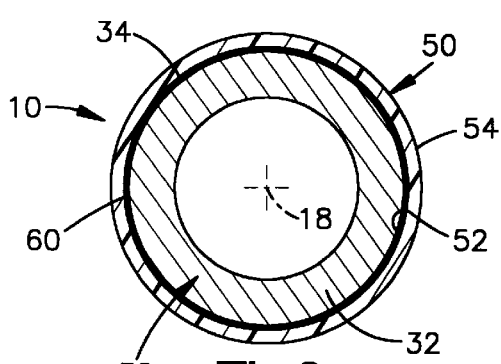
FIG. 3 is a sectional view taken along line 3—3 of FIG. 2.
Figure 4:
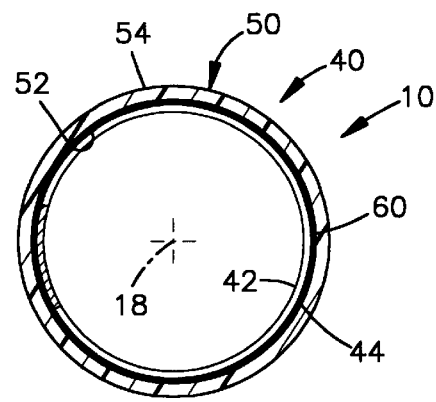
FIG. 4 is a sectional view taken along line 4—4 of FIG. 2.

The sleeve 50 is bonded to the rigid drive shaft section 30 and to the flexible drive shaft section 40 by a polymer adhesive 60 (FIG. 3). The polymer adhesive 60 is preferably one that is cured at room temperature. The polymer adhesive 60 may be one that is cured at a higher temperature, provided that the curing temperature of the adhesive does not exceed the relaxation temperature of the cold worked metal of the flexible drive shaft section 40.

The drive shaft 16 also includes a second rigid drive shaft section 70 which includes a proximal end portion 72 having a cylindrical outer surface 74. The proximal end portion 72 of the second rigid drive shaft section 70 is connected by a plastic sleeve 80 for rotation with the distal end portion 46 of the flexible drive shaft section 40. The sleeve 80 is preferably made from the same material and has the same construction as the sleeve 50. Specifically, the sleeve 80 has a hollow cylindrical configuration including parallel, cylindrical inner and outer surfaces 82 and 84. The inner surface 82 of the sleeve 80 is bonded to the outer side surface 74 of the proximal end portion 72 of the second rigid drive shaft section 70 and to the outer side surface 48 of the distal end portion 46 of the flexible drive shaft section 40.

The sleeve 80 is bonded to the second rigid drive shaft section 70 and to the flexible drive shaft section 40 by a layer of polymer adhesive 88. The polymer adhesive 88 is preferably the same as the adhesive 60 which is used to bond the sleeve 50.

A cutting tip 90 is fixed for rotation with the second rigid drive shaft section 70. The cutting tip 90 may be formed as one piece with the second rigid drive shaft section 70.

Because of the efficiency of a sleeve in transmitting torsional load, the sleeves 50 and 80 may be very thin. A sleeve 50 or 80 having a wall thickness of only 0.001 inch can carry a torsional load of 10 inch-pounds.

FIGS. 5 and 6 illustrate a surgical instrument 10a in accordance with a second embodiment of the present invention. The surgical instrument 10a is generally similar in construction to the surgical instrument 10 (FIGS. 1–4), and parts which are the same are given the same reference numeral with the suffix "a" added.

In the surgical instrument 10a, the distal end portion 32a of the rigid drive shaft section 30a is counter-bored to form a projecting tubular member. The proximal end portion 72a of the second rigid drive shaft section 70a is counter-bored to form a projecting tubular member.

The proximal end portion 42a of the flexible drive shaft section 40a is received within and is soldered to the inside of the tubular member 32a of the rigid drive shaft section 30a. The solder 100 may be any soldering material that has a melting temperature below the relaxation temperature of the cold-worked metal of the flexible driveshaft section 40a. The solder 100 is an adhesive material, that is, it adheres or bonds together to two parts 42a and 32a.

In a similar manner, the distal end portion 46a of the flexible drive shaft section 40a is received within and is soldered to the inside of the tubular member 72a on the second rigid drive shaft section 70a.

Instead of being soldered, the end portions 42a and 46a of the flexible drive shaft section 40a may be secured to the rigid drive shaft sections 32a and 72a by the polymer adhesive which is used to bond the plastic sleeves 50 and 80 in the surgical instrument 10 (FIGS. 1–4).

The advantages of the present invention include:

(1) Because none of the joints are welded, the high heat levels associated with welding are not experienced during the formation of the joints between the rigid and flexible drive shaft sections. Therefore, the material strength of the cold-worked metal spring is not degraded.

(2) Because of the lack of high heat, there is no relaxation of the spring material during the bonding of the joints. Thus, the flexible drive shaft section remains in its desired configuration.

(3) The joints formed with plastic sleeves can transfer twice as much torque, or more, as compared with welded joints.

(4) The assembly of each joint requires a minimum of hardware and equipment. Standard materials, including plastic tubing sleeves, polymer adhesive and solder, can be used.

(5) The expensive equipment needed to weld such small joints is not needed.

From the above description of the invention, those skilled in the art will perceive improvements, changes and modifications in the invention. For example, the two joints at opposite ends of the flexible drive shaft section can be secured in two different ones of the illustrated or described manners. Also, when a polymer adhesive is used, the rigid tubular drive shaft sections may be either metal or plastic. Such improvements, changes and modifications within the skill of the art are intended to be covered by the appended claims.

Having described the invention, we claim:

1. A surgical instrument drive shaft comprising:
   a rigid drive shaft section having an end portion;
   a flexible drive shaft section comprising a bendable spring having an outer surface and an end portion;
   a sleeve for transmitting torque between said rigid drive shaft section and said bendable spring, said sleeve having an inner surface and extending from said end portion of said rigid drive shaft section over said end portion of said flexible drive shaft section, said inner surface of said sleeve being disposed radially outward of said outer surface of said bendable spring; and
   an adhesive material disposed radially between said inner surface of said sleeve and said outer surface of said bendable spring and joining said inner surface of said sleeve to said outer surface of said bendable spring, whereby said sleeve is disposed in a torque-transmitting relationship between said rigid drive shaft section and said bendable spring.

2. A surgical instrument drive shaft as set forth in claim 1 wherein said bendable spring is made of a cold-worked metal.

3. A surgical instrument drive shaft as set forth in claim 2 wherein said sleeve is made of metal.

4. A surgical instrument drive shaft as set forth in claim 3 wherein said adhesive material is a solder having a melting temperature below the relaxation temperature of said bendable metal spring.

5. A surgical instrument drive shaft as set forth in claim 3 wherein said adhesive material is a polymer cured at a temperature below the relaxation temperature of said bendable metal spring.

6. A surgical instrument drive shaft as set forth in claim 5 wherein said polymer is cured substantially at room temperature.

7. A surgical instrument drive shaft as set forth in claim 2 wherein said sleeve is made of a thin-walled plastic and said adhesive is a polymer cured at a temperature below the relaxation temperature of said bendable metal spring.

8. A surgical instrument drive shaft as set forth in claim 7 wherein said polymer is cured substantially at room temperature.

9. A surgical instrument drive shaft as set forth in claim 1 wherein said sleeve is a tubular member formed as one piece with said end portion of said rigid drive shaft section.

10. A surgical instrument drive shaft as set forth in claim 9 wherein said tubular member is made of metal and said adhesive is a solder having a melting temperature below the relaxation temperature of said bendable metal spring.

11. A surgical instrument drive shaft as set forth in claim 1 wherein said sleeve is a tubular member formed separately from said rigid drive shaft section, said rigid drive shaft section has an outer surface and said adhesive material joins said inner surface of said sleeve to said outer surface of said rigid drive shaft section.

12. A surgical instrument drive shaft as set forth in claim 11 wherein said sleeve is made of thin-walled plastic and said adhesive is a polymer cured at a temperature below the relaxation temperature of said bendable metal spring.

13. A surgical instrument drive shaft as set forth in claim 12 wherein said bendable spring is made of cold worked stainless steel.

* * * * *